United States Patent
Hashiguchi et al.

(10) Patent No.: US 7,365,187 B2
(45) Date of Patent: Apr. 29, 2008

(54) DNA AMPLIFICATION METHOD AND KIT THEREFOR

(75) Inventors: Satoshi Hashiguchi, Kyoto (JP); Ken Inose, Kyoto (JP)

(73) Assignee: Arkray, Inc., Kyoto-shi, Kyoto (JP)

( * ) Notice: Subject to any disclaimer, the term of this patent is extended or adjusted under 35 U.S.C. 154(b) by 0 days.

(21) Appl. No.: 10/547,354

(22) PCT Filed: Mar. 5, 2004

(86) PCT No.: PCT/JP2004/002896

§ 371 (c)(1),
(2), (4) Date: Aug. 29, 2005

(87) PCT Pub. No.: WO2004/079009

PCT Pub. Date: Sep. 16, 2004

(65) Prior Publication Data

US 2006/0188881 A1    Aug. 24, 2006

(30) Foreign Application Priority Data

Mar. 7, 2003    (JP) .............................. 2003-061841

(51) Int. Cl.
*C07H 21/04*    (2006.01)
*C12Q 1/68*    (2006.01)
*C12P 19/34*    (2006.01)

(52) U.S. Cl. ..................... 536/24.3; 435/6; 435/91.2

(58) Field of Classification Search ................ None
See application file for complete search history.

(56) References Cited

U.S. PATENT DOCUMENTS 5,928,905 A * 7/1999 Stemmer et al. ........... 435/91.1
6,716,580 B2 * 4/2004 Gold et al. .................... 435/6

FOREIGN PATENT DOCUMENTS

| EP | 1 020 534 | 7/2000 |
| WO | WO 96/41012 | 12/1996 |
| WO | WO 01/94638 | 12/2001 |
| WO | WO 02/06528 | 1/2002 |

OTHER PUBLICATIONS

Chae et al. Chromosomal assignment of short cDNA sequences by PCR using overlapping and tailed short primers. (1994) DNA Res. 1:149-155.*
International Search Report dated Mar. 30, 2004.
Notomi, et al. "Loop-mediated Isothermal Amplification of DNA," *Nucleic Acids Research*, vol. 28, No. 12, pp. e63 i-vii, Jun. 2000.
Supplementary European Search Report, dated Apr. 21, 2006 and issued to a related European application.

* cited by examiner

*Primary Examiner*—Young J. Kim
*Assistant Examiner*—David C. Thomas
(74) *Attorney, Agent, or Firm*—Knobbe, Martens, Olson & Bear, LLP

(57) ABSTRACT

In a method for amplifying a DNA, comprising performing PCR using a sense primer and an antisense primer, PCR is performed in the presence of an additional sense primer comprising the sense primer and an oligodeoxyribonucleotide having a first additional sequence and ligated to the 5' end of the sense primer and an additional antisense primer comprising the antisense primer and an oligodeoxyribonucleotide having a second additional sequence complementary to the first additional sequence and ligated to the 5' end of the antisense primer; a Tm value of the additional sequences is lower than Tm values of the sense primer and the antisense primer; and annealing temperature in PCR is initially set to be a temperature at which the additional sequences do not anneal and changed in the course of PCR to a temperature at which the additional sequences anneal to each other.

8 Claims, 4 Drawing Sheets

DNA AMPLIFICATION METHOD AND KIT THEREFOR

RELATED APPLICATIONS

This is the U.S. National Phase under 35 U.S.C. § 371 of International Application PCT/JP2004/002896, filed Mar. 5, 2004, which was published in a language other than English, which claims priority of JP 2003-061841, filed Mar. 7, 2003.

TECHNICAL FIELD

The present invention relates to a method for amplifying a DNA and a kit therefor as well as a method for detecting a DNA using the DNA amplification method and a kit therefor.

BACKGROUND ART

Amplification of DNA such as genes is an important technique in genetic screening and so forth, and amplification methods using a DNA polymerase such as PCR and LAMP are known.

PCR is a DNA amplification method in which denaturation, annealing and extension of DNA are repeated by using a heat-resistant DNA polymerase and two kinds of primers with thermal cycles (for example, refer to Japanese Patent Publication (Kokoku) No. 4-67957).

LAMP is a DNA amplification method in which DNA is amplified at a constant temperature by using a strand displacement type DNA polymerase and four kinds of primers that recognize six regions (for example, refer to International Publication No. WO00/28082).

DISCLOSURE OF THE INVENTION

The conventional methods suffer from the following problems. As for PCR, the DNA amplification efficiency is twice per cycle at maximum in principle. As for LAMP, it is difficult to design primers.

Therefore, an object of the present invention is to provide a method for amplifying a DNA, which provides high amplification efficiency and for which primers can be easily designed.

The inventors of the present invention found that the aforementioned object could be achieved by using an additional primer pair having complementary sequences at the 5' ends in addition to a usual primer pair and changing a part of conditions in PCR, and thus accomplished the present invention.

The present invention provides the followings.
(1) A method for amplifying a DNA, comprising performing PCR using a sense primer and an antisense primer, wherein PCR is performed in the presence of an additional sense primer comprising the sense primer and an oligodeoxyribonucleotide having a first additional sequence and ligated to the 5' end of the sense primer and an additional antisense primer comprising the antisense primer and an oligodeoxyribonucleotide having a second additional sequence complementary to the first additional sequence and ligated to the 5' end of the antisense primer; a Tm value of the additional sequences is lower than Tm values of the sense primer and the antisense primer; and annealing temperature in PCR is initially set to be a temperature at which the additional sequences do not anneal and changed in the course of PCR to a temperature at which the additional sequences anneal to each other.
(2) The method according to (1), wherein the Tm value of the additional sequences is lower than the Tm values of the sense primer and the antisense primer by 5° C. or more.
(3) A kit used for the method according to (1), which comprises the additional sense primer comprising the sense primer and the oligodeoxyribonucleotide having the first additional sequence and ligated to the 5' end of the sense primer and the additional antisense primer comprising the antisense primer and the oligodeoxyribonucleotide having the second additional sequence complementary to the first additional sequence and ligated to the 5' end of the antisense primer, wherein the Tm value of the additional sequences is lower than the Tm values of the sense primer and the antisense primer.
(4) The kit according to (3), wherein the Tm value of the additional sequences is lower than the Tm values of the sense primer and the antisense primer by 5° C. or more.
(5) A method for detecting an objective DNA, which comprises amplifying the objective DNA by the method according to (1) and detecting an amplification product.
(6) The method according to (5), wherein the detecting is performed by real time PCR.
(7) A kit used for the method according to (5), which comprises the additional sense primer comprising the sense primer and the oligodeoxyribonucleotide having the first additional sequence and ligated to the 5' end of the sense primer and the additional antisense primer comprising the antisense primer and the oligodeoxyribonucleotide having the second additional sequence complementary to the first additional sequence and ligated to the 5' end of the antisense primer, wherein the Tm value of the additional sequences is lower than the Tm values of the sense primer and the antisense primer.
(8) The kit according to (7), which comprises a probe for real time PCR.

According to the present invention, PCR can be performed in a manner similar to that of usual PCR except that a pair of additional primers having oligodeoxyribonucleotides of complementary sequences at the 5' ends is additionally used, and primers can be more easily designed compared with LAMP. Further, because amplification products are linked via the additional portions of the additional primers, the amplified sequence increases at a rate higher than twice per cycle. Since the amplification efficiency increases, reduction of time for real time detection using a probe and increase of signals can be expected. Further, no special apparatus is additionally required other than an apparatus necessary for usual PCR.

BEST MODE FOR CARRYING OUT THE INVENTION

Figure 1:
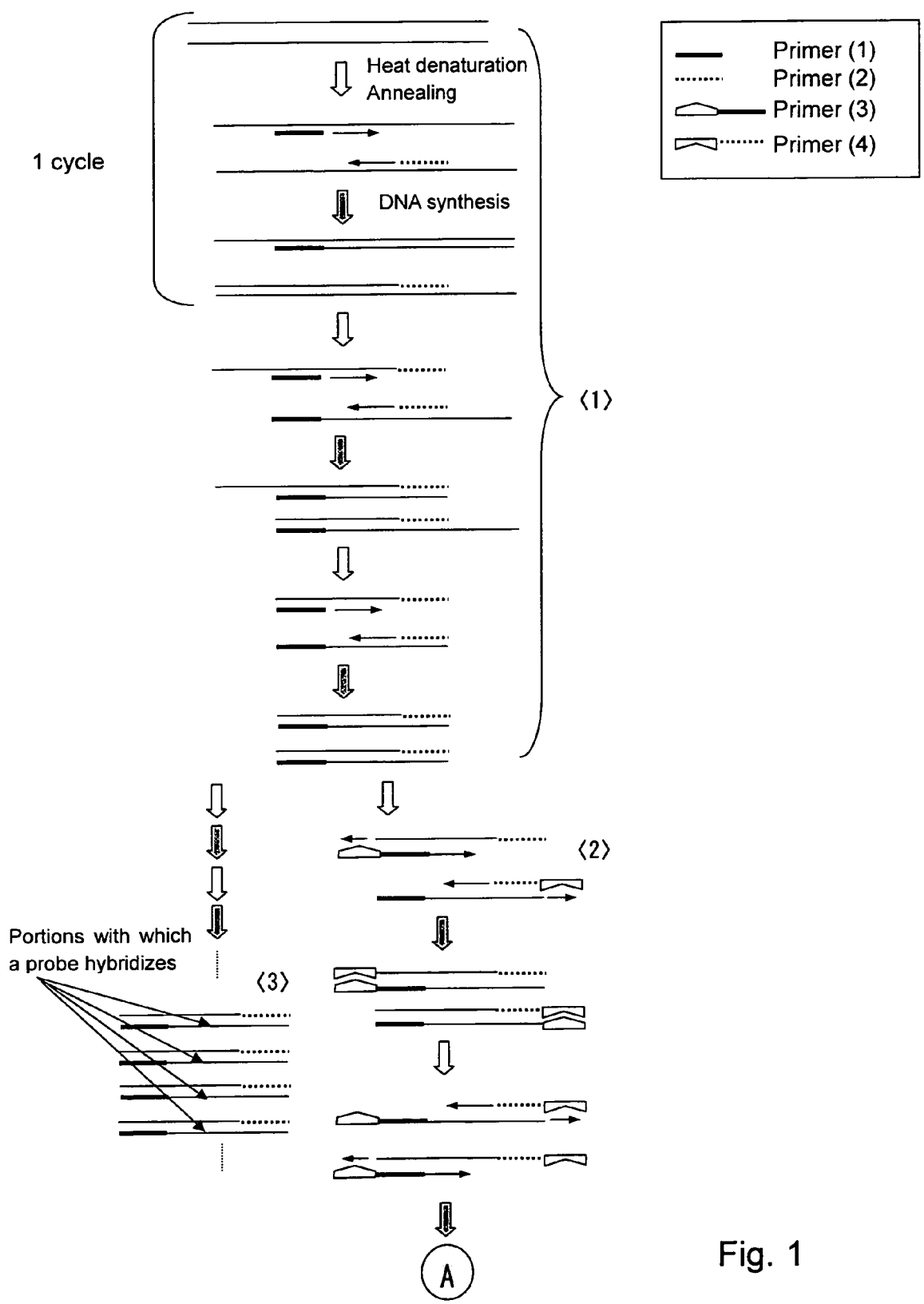
FIGS. 1 to 3 are explanatory diagrams of the principle of the method of the present invention.

In the present specification, the terms "sense" and "antisense" are used to indicate relative relationship between one chain and a chain complementary thereto of a double-stranded DNA, and the sense chain does not necessarily refer to a chain having a nucleotide sequence identical to that of the transcription product. Further, the Tm value is a value obtained by the nearest neighbor base pair analysis.

<1> Amplification Method of the Present Invention and Kit Therefor

The amplification method of the present invention is a method for amplifying a DNA by PCR using a sense primer and an antisense primer, and is characterized in that PCR is performed in the presence of an additional sense primer comprising the sense primer and an oligodeoxyribonucleotide having a first additional sequence and ligated to the 5' end of the sense primer and an additional antisense primer comprising the antisense primer and an oligodeoxyribonucleotide having a second additional sequence complementary to the first additional sequence and ligated to the 5' end of the antisense primer; a Tm value of the additional sequences is lower than Tm values of the sense primer and the antisense primer; and annealing temperature in PCR is initially set to be a temperature at which the additional sequences do not anneal and changed in the course of PCR to a temperature at which the additional sequences anneal to each other.

The amplification method of the present invention usually comprises the following steps.

(a) Step of providing a template, a sense primer, an antisense primer, an additional sense primer comprising the sense primer and an oligodeoxyribonucleotide having a first additional sequence and ligated to the 5' end of the sense primer and an additional antisense primer comprising the antisense primer and an oligodeoxyribonucleotide having a second additional sequence complementary to the first additional sequence and ligated to the 5' end of the antisense primer. In this step, the aforementioned additional sequences are designed so that the Tm value of the additional sequences should be lower than the Tm values of the sense primer and the antisense primer.

(b) Step of performing PCR using the template, the sense primer and the antisense primer in the presence of the additional sense primer and the additional antisense primer. In this step, the annealing temperature is initially set to be a temperature at which the aforementioned additional sequences do not anneal and changed in the course of PCR to a temperature at which the aforementioned additional sequences anneal to each other.

The amplification method of the present invention can be performed according to a usual PCR method except that an additional primer pair consisting of the additional sense primer and the additional antisense primer is used, and that the annealing temperature is lowered in the course of PCR.

The primer pair comprising the sense primer and the antisense primer can be designed in the same manner as in a method of designing primers for usual PCR. The lengths and Tm values of the sense primer and the antisense primer are usually 15-mer to 40-mer and 50 to 72° C., preferably 25-mer to 32-mer and 55 to 70° C. The lengths of the sense primer and the antisense primer may not be identical. However, it is preferable that the Tm values of the sense primer and the antisense primer are almost the same (the difference is usually not more than 2° C.).

The additional sense primer is obtainable by ligating an oligodeoxyribonucleotide having the first additional sequence to the 5' end of the sense primer, and the additional antisense primer is obtainable by ligating an oligodeoxyribonucleotide having the second additional sequence complementary to the first additional sequence to the 5' end of the antisense primer. An intervening sequence may exist between the additional sequence and the sense or antisense primer sequence so long as the effect of the amplification method of the present invention can be obtained. Usually, a sequence of 1 to 10 nucleotides may exist. The length of this intervening sequence may be different in the additional sense primer and the additional antisense primer.

The first additional sequence usually has a length of 15-mer to 30-mer and a Tm value of 45 to 67° C., preferably a length of 18-mer to 23-mer and a Tm value of 50 to 65° C. Because the second additional sequence is complementary to the first additional sequence, the length and Tm value of the second additional sequence are identical to those of the first additional sequence. The Tm value of the additional sequences is lower than the Tm values of the sense primer and the antisense primer (if the Tm values thereof are different, comparison is made for the lower Tm), preferably by 5° C. or more. Except that the additional sequences should have the Tm value as described above, they can be designed in the same manner as in designing of usual primers taking into account requirements such as avoidance of a sequence that may form an intramolecular higher-order structure.

The ratio of the additional sense primer and the additional antisense primer is preferably 1:1 (molar ratio).

The amount of the additional primer pair comprising the additional sense primer and the additional antisense primer is usually 0.1 to 1 time with respect to the amount of the primer pair comprising the sense primer and the antisense primer.

PCR is performed by repeating denaturation of a double-stranded DNA to obtain single-stranded DNAs (denaturation step), annealing a primer to the single-stranded DNA (annealing step) and extending the chain in the direction from the 3' end of the primer with a DNA polymerase (extension step).

In the amplification method of the present invention, the annealing temperature is set at the initial stage of PCR to be a temperature at which the aforementioned additional sequences do not anneal and changed in the course of PCR to a temperature at which the aforementioned additional sequences anneal to each other.

These steps can be performed by using one reaction mixture in a thermal cycler in the same manner as usual PCR.

A typical example of the composition of the PCR reaction mixture is as follows.

TABLE 1

| DNA fragments (template) | $10^2$ to $10^5$ molecules, or 1 to 1000 ng/µl |
|---|---|
| Primers | 200 to 1000 nM |
| Additional primers | 200 to 1000 nM |
| Nucleotides | 200 µM each |
| DNA polymerase | 0.5 to 2.5 U/µl |
| Tris-HCl (pH 7 to 8) | 10 to 20 mM |
| $MgCl_2$ | 1.5 to 5 mM |
| KCl | 50 to 100 mM |
| Surfactant or gelatin | 0.1 to 2% |
| (Final volume: 25 to 100 µl) | |

Further, a typical example of the temperature cycle is as follows. This temperature cycle is usually repeated 25 to 35 times.

Figure 2:
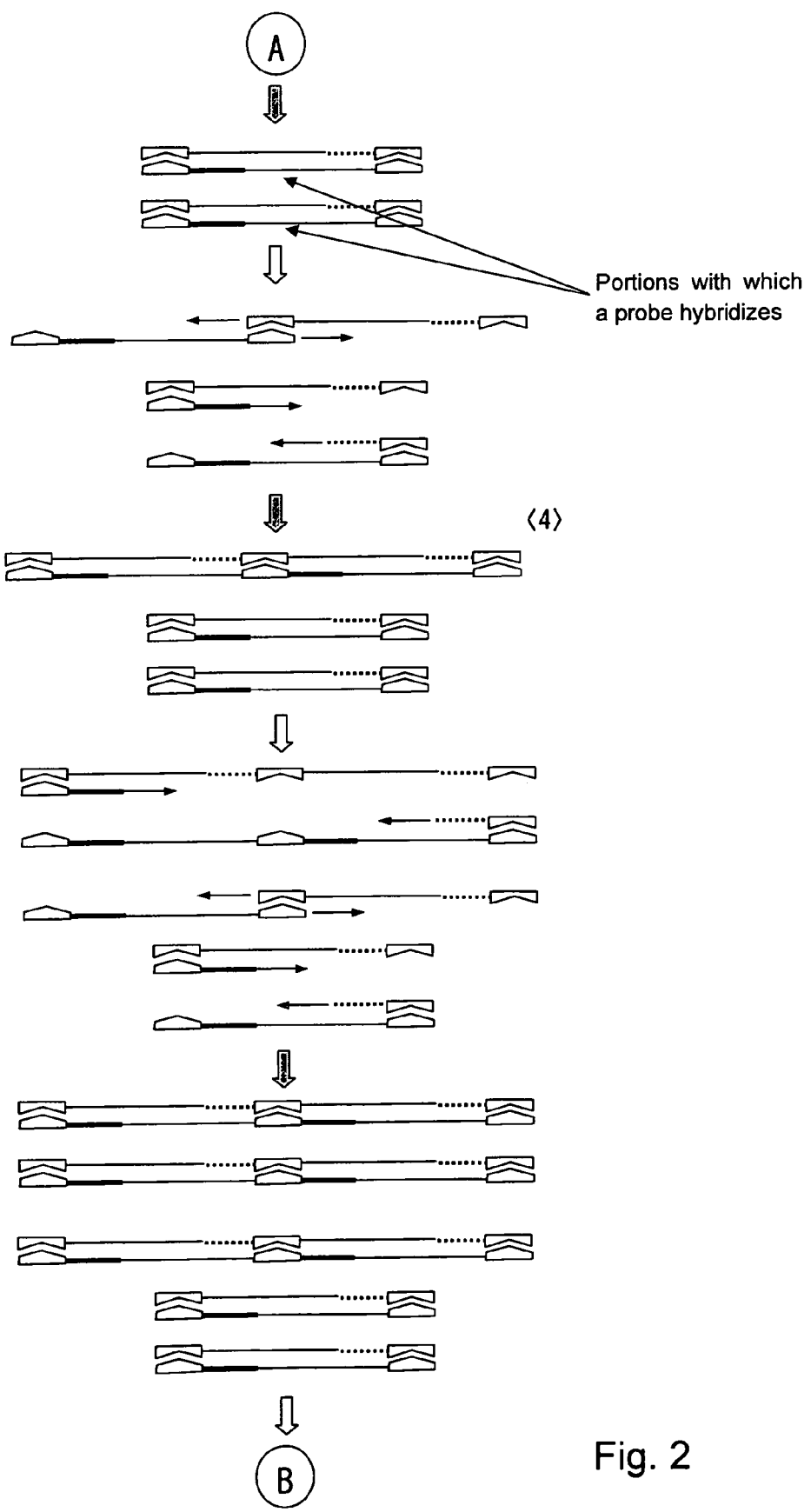
Figure 3:
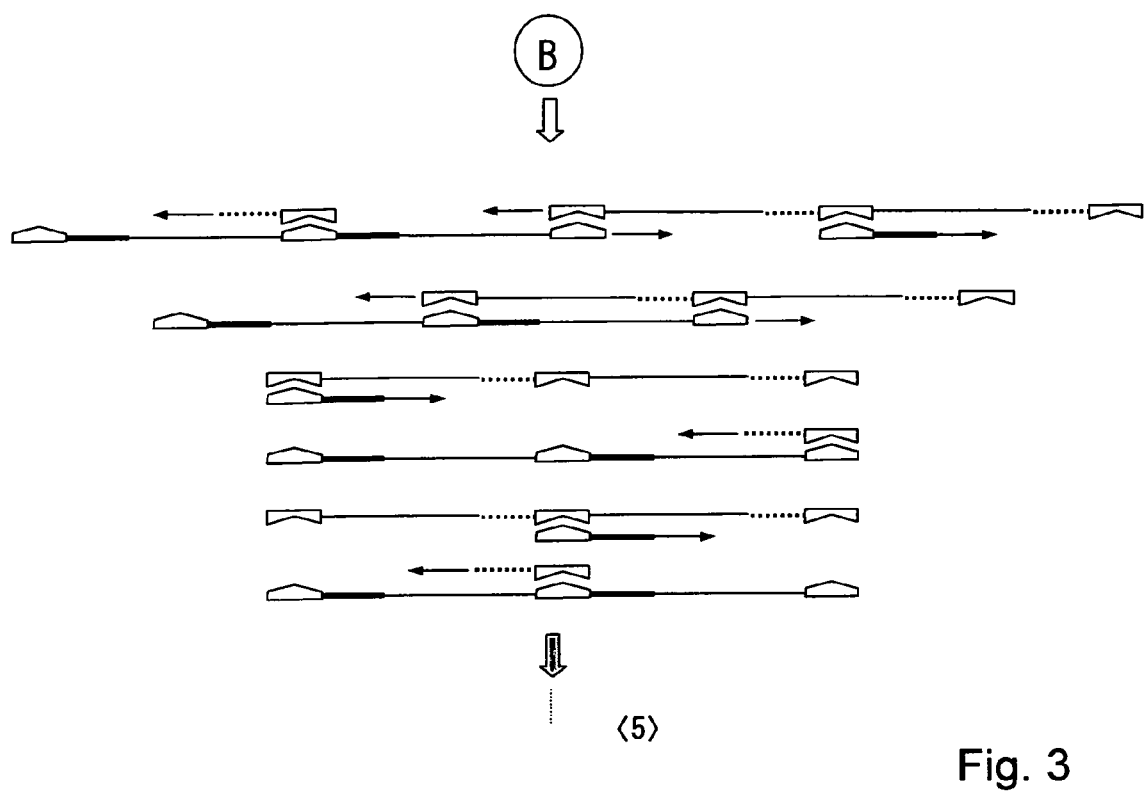

(1) Denaturation: 94 to 98° C. for 10 to 30 seconds
(2) Annealing: for initial stage (usually the first 5 to 15 cycles), 60 to 95° C. for 10 to 30 seconds, and for later stage, 50 to 65° C. for 10 to 30 seconds
(3) Extension: 70 to 74° C. for 20 to 60 seconds The principle of the amplification method of the present invention will be explained with reference to FIGS. 1 to 3.

Primers (1) and (2) are designed as the sense primer and the antisense primer on the basis of a target sequence. Further, primers (3) and (4) are designed as the additional sense primer and the additional antisense on the basis of the designed primers (1) and (2). The primer (3) is obtained by adding a first additional sequence (additional sequence 1) to the 5' end of the primer (1), and the primer (4) is obtained by adding a second additional sequence (additional sequence 2) to the 5' end of the primer (2). The additional sequence 1 and the additional sequence 2 are complementary to each other.

Because annealing is performed at temperature at which the additional sequences do not anneal at the initial stage of PCR, a target site (monomer) is amplified by PCR (<1> in FIG. 1). Since the additional monomer has an additional sequence, it hardly anneals to the initial template DNA including the target site as a part thereof. However, as the monomer increases in number, the additional primers also start to anneal (<2> in FIG. 1). During this process (and after change of the annealing temperature), amplification of the monomer with the primers (1) and (2) also proceeds until the reaction reaches a plateau (<3> in FIG. 1).

When the annealing temperature is changed to a temperature at which the additional sequences anneal to each other, annealing of the additional sequences occurs. The strands of a hybrid produced by annealing of single-stranded DNAs with the additional sequences at the ends function as a primer and a template to produce a double-stranded DNA (ligation product, <4> in FIG. 2). Further, the additional primers can hybridize to a single-stranded DNA of the ligation product, and a hybrid obtained by this hybridization also produces a double-stranded DNA. Because such various reactions can occur, the overall reaction hardly reaches a plateau, and thus the objective sequence is amplified into a larger amount than that obtainable by performing usual PCR (<5> in FIG. 3). Therefore, if a detection method using a probe specific to the objective sequence is employed, the portion to which the probe should hybridize is amplified into a large amount, and thus a strong signal can be obtained (<3> in FIG. 1 and <4> in FIG. 2).

The present invention also provides a kit used for the amplification method of the present invention (amplification kit of the present invention). This kit is characterized by including the aforementioned additional sense primer and additional antisense primer.

These additional sense primer and additional antisense primer are as described above in the explanation of the amplification method of the present invention.

The amplification kit of the present invention may include a reagent required for performing PCR in addition to the additional sense primer and the additional antisense primer.

In the amplification kit of the present invention, the primers and other reagents may be included separately, or a part of them may be included as a mixture.

<2> Detection Method of the Present Invention and Kit Therefor

The detection method of the present invention comprises amplification of an objective DNA by the amplification method of the present invention and detection of the amplification product.

In the detection method of the present invention, the amplification product can be detected according to a usual method for detecting an amplification product. However, because the number of the objective sequence in one molecule of the amplification product is not constant, it is preferable to use a detection method specific to the objective sequence. For example, the detection may be performed by real time PCR, in which PCR is performed in the presence of an oligonucleotide labeled with a fluorescent dye so that fluorescence should change when it binds to an amplification product (for example, a hybridization probe designed so that it should hybridize to a single-stranded DNA, and fluorescence intensity thereof should change when it hybridizes etc.), and fluorescence is measured.

Because the amplification efficiency of the objective sequence increases in the amplification method of the present invention, it is preferable to use a detection method that is dependent on the number of the objective sequence. Examples of such a detection method include, for example, real time detection using a probe. The real time detection using a probe is expected to reduce the detection time and increase the signal.

The present invention also provides a kit for the detection method of the present invention (the detection kit of the present invention). This kit is characterized by including the aforementioned additional sense primer and additional antisense primer.

These additional sense primer and additional antisense primer are as described above in the explanation of the amplification method of the present invention.

The detection kit of the present invention may further include a reagent required for performing PCR and/or detection of the amplification product in addition to the additional sense primer and the additional antisense primer. The detection kit of the present invention preferably includes a probe for real time detection.

In the detection kit of the present invention, the primers and other reagents may be separately included, or a part of them may be included as a mixture.

EXAMPLES

Hereafter, the present invention will be explained more specifically with reference to the following example.

Example 1

Detection of Cryptic Plasmid pLGV440 of *Chlamydia* (*Chlamydia trachomatis*)

Primers (1) to (4) and a probe having the nucleotide sequences listed below were prepared on the basis of the known nucleotide sequence of the cryptic plasmid pLGV440 of *Chlamydia* (GenBank accession number X06707). The additional sequence 1 and the additional sequence 2 in the primers (3) and (4) were complementary to each other. The Tm values of the primers (1) and (2) were 65° C. and 64.8° C., respectively. The Tm value of the additional sequences was 60.6° C. The Tm values used here were obtained by the nearest neighbor base pair analysis. The 5' end of the probe was labeled with BODIPY FL (Molecular Probe) by a usual method.

TABLE 2

Primers
(1): AGCTCTGGGAGCATGTTCTTAGTCTCAGCAG (SEQ ID NO: 1, corresponding to the nucleotide numbers 5171 to 5200 of X06707)
(2): TCGCGTAGGGCTTAGAATCACCTTCTCGTAC (SEQ ID NO: 2, corresponding to the nucleotide numbers 5276 to 5246 of X06707)
(3): CCTGATCAGGGTGCTTGCGAGAGCTCTGGGAGCATGTTCTTAGTCTCAGCAG (SEQ ID NO: 3, additional sequence 1 + (1))
(4): CTCGCAAGCACCCTGATCAGGTCGCGTAGGGCTTAGAATCACCTTCTCGTAC (SEQ ID NO: 4, additional sequence 2 + (2))
Probe
(BODIPY FL)-CAAAGCTAGAACAACGCCGCCTTCCATTCTTGATGC-(phosphorylated) (SEQ ID NO: 5, corresponding to the nucleotide numbers 5245 to 5210 of X06707)

Genomic DNA of *Chlamydia* isolated and purified from the ATCC strain CT-VR878 by a usual method was used as a template to amplify the DNA with the following composition of reaction mixture and reaction conditions.

TABLE 3

| Composition of reaction mixture | |
|---|---|
| H$_2$O | 18.375 µl |
| 10× Gene Taq buffer | 2.5 µl |
| 2.5 mM each of ATP, UTP, GTP, CTP | 2 µl |
| Probe (5 µM) | 0.5 µl |
| Primer (1) (100 µM) | 0.125 µl |
| Primer (2) (100 µM) | 0.125 µl |
| Primer (3) (100 µM) | 0.125 µl |
| Primer (4) (100 µM) | 0.125 µl |
| Gene Taq (5 U/µl) | 0.125 µl |
| Genomic DNA (200 copies) | 1 µl |
| Final volume | 25 µl |

*Gene Taq (Nippon Gene)

TABLE 4

Reaction conditions

95° C. for 1 min
(95° C. for 15 sec, 67° C. for 15 sec, 72° C. for 30 sec) × 10 cycles
(95° C. for 15 sec, 62° C. for 15 sec, 72° C. for 30 sec) × 40 cycles
72° C. for 3 min At the steps of the reactions at 67° C. for 15 seconds and 62° C. for 15 seconds, fluorescence (excitation: 495 nm, detection: 525 nm) was detected. Under these conditions, fluorescence quenches when the probe hybridizes with the amplification product, and therefore production of the amplification product can be detected as reduction of fluorescence intensity.

Further, amplification was also performed under the same conditions except that the primer (1) and (2) alone were used as primers.

Figure 4:
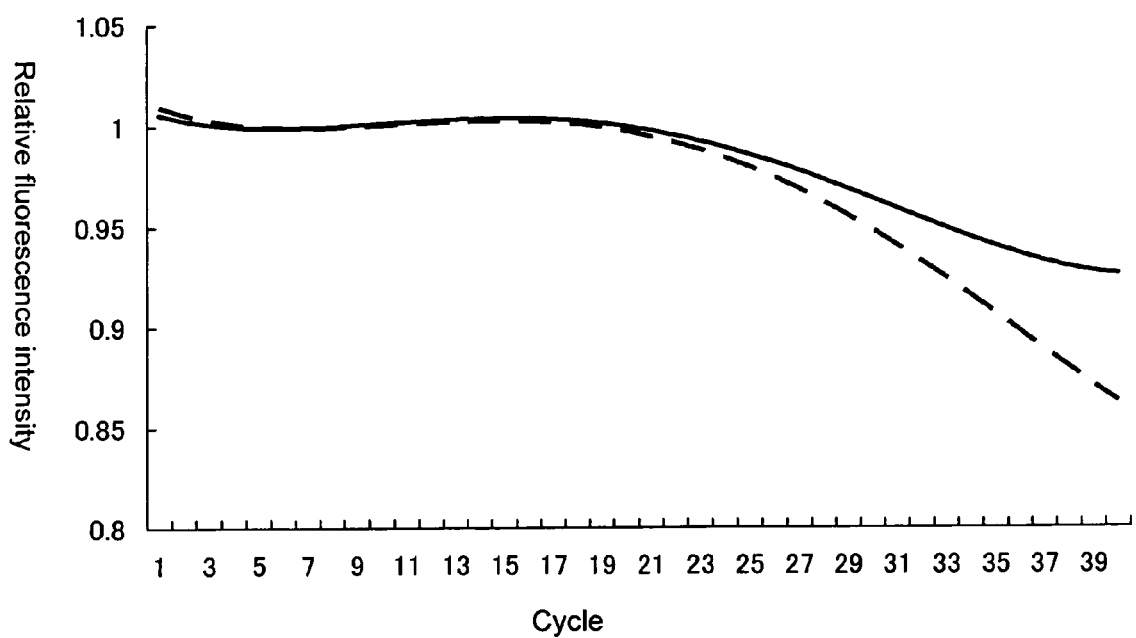
FIG. 4 shows a time course of production of amplification products. The dotted line shows the result obtained with usual primers+additional primers, and the solid line shows the result obtained with usual primers alone.

The results are shown in FIG. 4. The dotted line represents the result obtained by using the primers (1) to (4) (usual primers+additional primers), and the solid line represents the result obtained by using the primers (1) and (2) alone (usual primers alone). These results revealed that production of the amplification product was increased by using the primers (3) and (4) in addition to the primers (1) and (2). Therefore, it is evident that the presence or absence of the cryptic plasmid pLGV440 can be determined with higher sensitivity.

INDUSTRIAL APPLICABILITY

There is provided a method for amplifying a DNA, which exhibits high amplification efficiency and for which primers can be easily designed.

What is claimed is:

1. A kit which comprises:
   a first sense primer,
   a first antisense primer,
   a second sense primer comprising the first sense primer and an oligodeoxyribonucleotide comprising a first additional sequence which is ligated to the 5' end of the first sense primer, and
   a second antisense primer comprising the first antisense primer and an oligodeoxyribonucleotide comprising a second additional sequence fully complementary to the first additional sequence which is ligated to the 5' end of the first antisense primer,
   wherein the $T_m$ value of the additional sequences is lower than the $T_m$ values of the first sense primer and the first antisense primer, and
   wherein the additional sequences have a length of 15 to 30 nucleotides.

2. The kit according to claim 1, wherein the $T_m$ value of the additional sequences is lower than the $T_m$ values of the first sense primer and the first antisense primer by 5° C. or more.

3. A method for amplifying DNA using the kit of claim 1, comprising performing PCR using the first sense primer and the first antisense primer, wherein PCR is performed in the presence of the second sense primer comprising the first sense primer and the oligodeoxyribonucleotide comprising the first additional sequence which is ligated to the 5' end of the first sense primer and the second antisense primer comprising the first antisense primer and the oligodeoxyribonucleotide comprising the second additional sequence fully complementary to the first additional sequence which is ligated to the 5' end of the first antisense primer;
   wherein the $T_m$ value of the additional sequences is lower than the $T_m$ values of the first sense primer and the first antisense primer;
   wherein the additional sequence have a length of 15 to 30 nucleotides; and
   wherein the annealing temperature in PCR is initially set to a temperature at which the additional sequences do not anneal and changed in the course of PCR to a temperature at which the additional sequences anneal to each other.

4. The method according to claim 3, wherein the $T_m$ value of the additional sequences is lower than the $T_m$ values of the first sense primer and the first antisense primer by 5° C. or more.

5. A method for detecting a target DNA, which comprises amplifying the target DNA by the method according to claim 3 and detecting the amplification product.

6. The method according to claim 5, wherein the detecting is performed by real-time PCR.

7. A kit used for the method according to claim 5, which comprises the second sense primer comprising the first sense primer and the oligodeoxyribonucleotide comprising the first additional sequence which is ligated to the 5' end of the first sense primer and the second antisense primer comprising the first antisense primer and an oligodeoxyribonucleotide comprising the second additional sequence fully complementary to the first additional sequence which is ligated to the 5' end of the first antisense primer, wherein the $T_m$ value of the additional sequences is lower than the $T_m$ values of the first sense primer and the first antisense primer.

8. The kit according to claim 7, which comprises a probe for real-time PCR.

* * * * *

UNITED STATES PATENT AND TRADEMARK OFFICE
CERTIFICATE OF CORRECTION

PATENT NO.         : 7,365,187 B2  
APPLICATION NO. : 10/547354  
DATED                 : April 29, 2008  
INVENTOR(S)       : Hashiguchi et al.

Page 1 of 1

It is certified that error appears in the above-identified patent and that said Letters Patent is hereby corrected as shown below:

Column 4, Line 24, "The amount of the additional" should be moved to Line 23 as

--(molar ratio). The amount of the additional--

Column 4, Line 67, "20 to 60 seconds" should be changed to --20 to 60 seconds.--

Column 10, Line 48, "the additional sequence" should be changed to --the additional sequences--

Column 10, Line 52, "not anneal" should be changed to --not anneal to each other--

Signed and Sealed this

Sixteenth Day of December, 2008

JON W. DUDAS  
*Director of the United States Patent and Trademark Office*

SEQUENCE LISTING

<160> NUMBER OF SEQ ID NOS: 5

<210> SEQ ID NO 1
<211> LENGTH: 31
<212> TYPE: DNA
<213> ORGANISM: Artificial Sequence
<220> FEATURE:
<223> OTHER INFORMATION: primer

<400> SEQUENCE: 1
agctctggga gcatgttctt agtctcagca g                                        31

<210> SEQ ID NO 2
<211> LENGTH: 31
<212> TYPE: DNA
<213> ORGANISM: Artificial Sequence

```
<220> FEATURE:
<223> OTHER INFORMATION: primer

<400> SEQUENCE: 2
tcgcgtaggg cttagaatca ccttctcgta c                                              31

<210> SEQ ID NO 3
<211> LENGTH: 52
<212> TYPE: DNA
<213> ORGANISM: Artificial Sequence
<220> FEATURE:
<223> OTHER INFORMATION: primer

<400> SEQUENCE: 3
cctgatcagg gtgcttgcga gagctctggg agcatgttct tagtctcagc ag                       52

<210> SEQ ID NO 4
<211> LENGTH: 52
<212> TYPE: DNA
<213> ORGANISM: Artificial Sequence
<220> FEATURE:
<223> OTHER INFORMATION: primer

<400> SEQUENCE: 4
ctcgcaagca ccctgatcag gtcgcgtagg gcttagaatc accttctcgt ac                       52

<210> SEQ ID NO 5
<211> LENGTH: 36
<212> TYPE: DNA
<213> ORGANISM: Artificial Sequence
<220> FEATURE:
<223> OTHER INFORMATION: probe

<400> SEQUENCE: 5
caaagctaga acaacgccgc cttccattct tgatgc                                         36
```